United States Patent [19]

Nichols

[11] Patent Number: 5,223,251
[45] Date of Patent: Jun. 29, 1993

[54] SKIN FRAGRANCE COMPOSITIONS

[75] Inventor: Larry D. Nichols, Arlington, Mass.

[73] Assignee: Purepac, Inc., Elizabeth, N.J.

[21] Appl. No.: 875,199

[22] Filed: Apr. 24, 1992

Related U.S. Application Data

[63] Continuation of Ser. No. 619,722, Nov. 29, 1990, abandoned, which is a continuation-in-part of Ser. No. 358,690, May 30, 1989, Pat. No. 5,000,947.

[51] Int. Cl.$^5$ .................. A61K 7/035; A61K 9/14; A61K 7/46
[52] U.S. Cl. .................. 424/69; 424/488; 424/489; 424/499; 514/281; 514/873; 512/4
[58] Field of Search .............. 424/401, 488, 489, 69; 512/4, 27, 1

[56] References Cited

U.S. PATENT DOCUMENTS

| | | | |
|---|---|---|---|
| 2,891,946 | 6/1959 | Volberg et al. | 260/230 |
| 3,557,083 | 1/1971 | Sacco | 260/230 |
| 3,824,085 | 7/1974 | Teno et al. | 44/78 |
| 3,846,404 | 11/1974 | Nichols | 260/230 |
| 3,940,384 | 2/1976 | Teno et al. | 260/226 |
| 3,985,298 | 10/1976 | Nichols | 239/54 |
| 4,016,254 | 4/1977 | Seager | 423/33 |
| 4,024,073 | 5/1977 | Shimizu et al. | 252/316 |
| 4,029,726 | 6/1977 | Nichols | 264/41 |
| 4,067,824 | 1/1978 | Teno et al. | 252/522 |
| 4,128,507 | 12/1978 | Mitzner | 252/522 |
| 4,193,989 | 3/1980 | Teno et al. | 424/60 |
| 4,369,173 | 1/1983 | Causland et al. | 424/35 |
| 4,383,988 | 5/1983 | Teno et al. | 424/68 |
| 4,543,203 | 9/1985 | Licciardello et al. | 424/69 X |
| 4,597,960 | 7/1986 | Cohen | 424/28 |
| 4,643,856 | 2/1987 | Nichols | 264/41 |
| 4,690,786 | 9/1987 | Ninomiya et al. | 264/4.6 |
| 4,690,825 | 9/1987 | Won | 424/501 |
| 4,695,464 | 9/1987 | Aldermann | 424/449 |
| 4,708,821 | 11/1987 | Shimokawa et al. | 512/12 |
| 4,724,240 | 2/1988 | Abrutyn | 514/847 |
| 4,738,851 | 4/1988 | Schoenwald et al. | 424/488 |
| 4,752,496 | 6/1988 | Fellows et al. | 427/27 |
| 4,755,433 | 7/1980 | Patel et al. | 420/422 |
| 4,780,564 | 10/1988 | Sprecker et al. | 424/69 X |
| 5,000,947 | 3/1991 | Nichols | 424/69 |
| 5,013,473 | 5/1991 | Norbury et al. | 252/174.13 |
| 5,089,269 | 2/1992 | Noda et al. | 424/456 |

OTHER PUBLICATIONS

Moleculon, Inc., Form 10-K for FY ended Nov. 30, 1988, pp. 1-7.

Primary Examiner—Thurman K. Page
Assistant Examiner—Neil Levy
Attorney, Agent, or Firm—Thomas J. Engellenner; James E. Maslow

[57] ABSTRACT

Liquefiable powder compositions are disclosed for the delivery of fragrances. In particular, microporous cellulosic powders, such as cellulose acetates or nitrates, are disclosed as high liquid content vehicles for the delivery of fragrance preparations dissolved or dispersed in a liquid carrier. The resulting powders permit the application of the fragrance preparations by simply rubbing or otherwise applying the formulation onto the skin in such a manner that the powder liquefies and appears to vanish. Upon application, the frangible liquid loaded cellulosic powders break up into minute particles that do not pass easily beyond the initial layers of the skin, but do permit the slow release of the fragrance agent.

4 Claims, No Drawings

SKIN FRAGRANCE COMPOSITIONS

REFERENCE TO RELATED APPLICATION

This application is a continuation of U.S. Ser. No. 619,722 filed Nov. 29, 1990, abandoned, which is a continuation-in-part of U.S. Ser. No. 358,690 filed May 30, 1989, now U.S. Pat. No. 5,000,947.

BACKGROUND OF THE INVENTION

The technical field of this invention is the topical application of personal care agents and, in particular, methods and compositions for the application of fragrant products to the skin.

Application of fragrant skin products (e.g., perfumes and fragrances) to one's skin in order to become more attractive to others, or to enjoy a pleasantly fragrant local environment, is a long-standing practice. A wide range of preparations are available for this purpose, including perfumes, colognes, lotion and powders. The active ingredients in such preparations are typically natural or synthetic organic compounds of low to intermediate volatility; unsaturated esters, ketones and aldehydes are particularly common ingredients. Fragrant products normally contain tens or hundreds of individual components, some of which in pure form have pleasant odors, some unpleasant odors, and some almost no odor at all. Smell is a complex and highly evocative sense whose mastery demands both art and science.

Ideal compositions for use as skin fragrances should be readily portable, spill-resistant, easy and unobtrusive to apply, readily distributable over the skin, invisible on clothing, long lasting, and able to provide an undistorted rendition of the intended fragrance. Most skin fragrance preparations are liquids or powders which do not fully satisfy these requirements. Portable, essentially invisible liquids can readily be compounded to have diverse odor intensities, but they are easily spilled, and they announce their use by a strong odor burst which makes private use in public difficult or impossible. Alternatively, powders tend to be messy, and they can be seen on the skin and are highly visible on clothing. As well, they cannot be compounded with enough active ingredients to produce strong, long-lasting fragrances, and adsorption effects often hamper accurate rendition. There thus exists a need for fragrant skin products which offer a better combination of convenience, privacy of application, invisibility, and accurate, long-lasting rendition.

Details of the formation of cellulosic powders can be found in the above-referenced parent application, U.S. Ser. No. 358,690, filed May 30, 1989, and a commonly-owned, copending application entitled "Process For Producing Liquid-Loaded Powders", by Larry D. Nichols and John F. Cline, Attorney Docket No. MOE-014, filed contemporaneously herewith, both of which are incorporated herein by reference. A preferred liquid-loadable powder includes microporous cellulose triacetate prepared by the method of the above application, Attorney Docket No. MOE-014, entitled "Process For Producing Liquid-Loaded Powders".

In one technique, the liquefiable powders are formed by dissolving a cellulosic polymer and a pore-forming liquid in a volatile, polar solvent (e.g., a low molecular weight halogenated hydrocarbon, ester or diester) and then dispersively evaporating the solution, for example, by spray drying. Suitable volatile solvents for cellulosic polymers include methylene chloride, acetone, ethyl acetate, ethyl carbonate, methyl formate and the like. Methylene chloride is a preferred solvent when the cellulosic polymer is cellulose triacetate. Alternatively, other solvents, such as formic acid or the like, can be used and the resulting solution can be sprayed into a non-solvent such as methanol where the powder particles are then recovered by filtration and rinsing. The active agent can be incorporated into the solvent or introduced by liquid phase substitution after the powder is formed.

SUMMARY OF THE INVENTION

Liquefiable polymer powder compositions are disclosed for the delivery of fragrant products. In particular, microporous cellulosic powders, such as cellulose acetates or nitrates, are disclosed as high liquid content vehicles for the delivery of perfumes and fragrances to the skin. The resulting powders permit the application of fragrant preparations to the skin by rubbing (or otherwise dispersing) them in a manner which causes the powder to liquefy and disappear. This vanishing behavior occurs because, as a result of typical rubbing action imparted to the powder during application, a plurality of the liquid-loaded cellulosic particles breaks up into invisibly minute fragments. The fragmenting particles promptly release their liquid payload as a thin film, suitable for immediate but not overpowering delivery of fragrance. However, typically, not all of the powder is fragmented upon initial application, so that a portion of the powder particles retain their payload and may be fragmented upon subsequent rubbing action. Hence, the applied fragrance can be renewed at will without application of additional powder.

The cellulosic powders useful in the present invention can range from about one to about 500 microns in average diameter, preferably from about 5 to about 100 microns in average diameter, and typically are roughly microspherical in shape. They are further characterized by being microporous with interconnecting pores ranging in size from about one to about 500 nanometers and are capable of holding liquid payloads of active agents.

The cellulosic powder can be formed from cellulosic polymers chosen from the group of cellulose acetates, cellulose butyrates, cellulose nitrates, cellulose propionates, ethyl celluloses and discrete or molecular mixtures thereof. One preferred cellulosic powder is a polymeric powder of cellulose triacetate, having a (dry) acetyl content greater than about 42 percent. The liquid content of the cellulosic powders of the present invention can range from about 50 percent to about 95 percent by weight.

The cellulosic materials used in the preparation of these liquefiable powders are neither reactive nor chemically adsorptive toward typical fragrant components of a fragrant product. This provides the formulator with freedom to control rendition by the choice of constituents similar to the control exercized traditional formulation of liquid compositions. Yet compositions made in accordance with the present invention permit the delivery of effective amounts of skin fragrance without many of the problems normally associated with conventional liquid or powder formulations. By assisting in the unobtrusive application of readily portable fragrances, and by providing an invisible reservoir compatible with long-lasting and accurate rendition, the compositions of the present invention can improve the efficacy, convenience, and economy of fragrant skin products for personal use. Furthermore, the liquefiable powders employed in this invention can contain concentrations of active ingredients as high as 90 to 95%, as compared with the maximum of 10 to 20% that can be incorporated into conventional powders, such as talc.

Fragrances and other constituents which can be used in the practice of this invention include such materials of common practice as esters, alcohols, ketones, and aldehydes, linear, branched or cyclic, saturated or unsaturated, of low, intermediate or high molecular weight. The active ingredients employed may individually possess pleasant odors, or they may have odors which would be undesirable alone but which pleasantly modify other odors, or they may improve the persistence or rendition of other fragrant ingredients. The cellulosic matrix of the liquefiable powders is broadly compatible with a wide range of aqueous solutions, alcoholic solutions, and oils, and even when particular active ingredients such as low molecular weight aromatic esters could in pure form soften the cellulosic material, mixtures involving other active ingredients and excipients typically lead to a liquid-loaded powder with acceptable properties.

Solid components can be included in the fragrant powder compositions of this invention simply by dissolving them in other liquid components. Nonfragrant excipients can readily be included in the fragrant powder compositions of this invention, including materials such as diluents, emollients, pigments, pearls, and talcs. The utility of such materials in cosmetic and skin care products is not unique to liquefiable powders, and their purposes and manners of use will be obvious to those skilled in the perfume and cosmetic arts.

When liquid formulations containing typical fragrances are to be diluted or extended for use in liquefiable cellulosic powders, most standard topical and cosmetic liquids are suitable for use, including but not limited to mineral oils, silicone oils, fatty esters, fatty alcohols, as well as lower molecular weight alcohols, glycols and esters. Volatile alcohol-water mixtures can be used to provide a cool initial sensation and a controlled burst of odor, again following standard practice in the perfume art.

In various embodiments of the invention, the fragrant powder composition can be used directly in powdered form; or mixed with other powders such as talc or starch to provide a drier feel; or compacted into cakes; or blended with binders and shaped into bars or sticks. In all such embodiments, application of the material to the skin distributes it substantially in the form of an invisible, fragmented and liquefied powder, and thus provides an advantageous combination of prompt and prolonged action.

In another embodiment the fragrance-loaded frangible cellulosic microbeads can be formulated into a cream or lotion by admixture with a suitable liquid base. Without the use of potentially irritating surfactants or other stabilizers such creams are as stable as conventional stabilized emulsions. Liquefiable fragrant cellulosic powders are thus suitable for the preparation of stable, minimally irritating, hypoallergenic creams. Suitable liquid bases for cream or lotion embodiments include water, alcohol, mineral or silicone oils, volatile silicones, and moisturizing agents such as glycerine or propylene glycol.

Regardless of the embodiment, various additives can be mixed with the liquid-loaded particles (or liquid base) including, for example, talc, cornstarch, waxes, silicones, analgesics, cosmetics, fragrances, lubricants, emollients, moisturizers, medications and other personal care agents, colorants, pearlescent agents, and mixtures of such additives.

In the compacted cake embodiments, the liquid loaded powders can be compacted to packing densities ranging from about 55 percent to about 75 percent, more preferably from about 60 percent to about 70 percent of the void-free density of the combined materials to yield cakes that are dry and firm and yet readily permit transfer of the formulation to the skin by finger or brush.

Such compacted cakes can be obtained by applying a pressure ranging from about 50 to about 80 PSI to a cellulosic powder which has been appropriately loaded with a liquid payload of the active agent. In the absence of other additives, the resulting shaped articles have a compacted density ranging from about 0.55 to about 0.75 gm/cc.

Sticks or bars incorporating liquefiable powders with active agent payloads can be made by a variety of techniques. For example, sticks can be formulated by compounding a liquefiable powder with fatty alcohols, fatty acids, and/or salts of fatty acid anions with metallic or alkanolamine cations to produce a stick having a soap as the binding agent.

Alternatively, stick compositions can be formed by compounding a liquefiable powder with soft, water-soluble polymers, such as polyethylene glycols or polypropylene glycols, to produce a stick having a soluble wax as the binding agent. Sticks can also be made up by compounding a liquefiable powder with silicones or with blends of liquids and solids, such as salts and/or propylene glycols, to produce sticks having a thick or partially-solidified slurry as the binding agent. In yet another approach, sticks can be formed by compounding a liquefiable powder with a fusible wax, including fatty esters, silicone waxes, polyglycol waxes and aliphatic waxes, and then applying heat and pressure to produce sticks having a wax as the binding agent.

The above binding agents can be introduced directly, or as payload in a second portion of liquefiable powder to be blended with that carrying the active ingredient. Other methods of stick production will readily occur to those skilled in the art.

The invention will next be described in connection with certain exemplary methods and compositions. However, it should be clear that various additions, subtractions and changes can be made by those skilled in the art without departing from the spirit or scope of the invention. For example, various additives can be mixed together with the sunscreen loaded powder particles of the invention, including, for example, talc, cornstarch, waxes, silicones, cosmetics, fragrances, lubricants, emollients, moisturizers, medications and other personal care agents, as well as colorants, pearlescent agents, and mixtures of such additives. Regardless of the embodiment, various additives can be mixed with the liquid-loaded particles (or liquid base) including, for example, talc, cornstarch, waxes, silicones, analgesics, cosmetics, fragrances, lubricants, emollients, moisturizers, medications and other personal care agents, colorants, pearlescent agents, and mixtures of such additives.

In some applications, it may also be preferable to include a quantity of a dry cellulosic powder (e.g., less than 50 percent of the total cellulosic components) to provide additional structural integrity to the composition. The term "dry cellulosic powder" is used herein to describe powders whose internal pores are liquid-free or have a liquid content of less than 50 percent.

DETAILED DESCRIPTION OF THE PREFERRED EMBODIMENT

The examples below illustrate the preparation of liquefiable skin fragrance powders.

EXAMPLE 1

15 gm of CTA was dissolved in 900 gm of methylene chloride aided by moderate stirring for 1 hour. 85 grm of Fragrance "A" was added to the resulting clear solution and stirred until fully dispersed. Fragrance "A" is a highly concentrated test fragrance composed of 20.5% Aldo-66, 6.9% Dow Corning DC-200 Dimethieme, 20.6% Dow Corning DC-345 cyclic silicone liquid and 52% Firmenich Fragrance Oil 423-236/B. The solution was sprayed at 1000 PSI from a 0.0135 inch nozzle downward into a tower 100 cm in diameter and 300 cm tall through which 1250 liters per minute of solvent-free air was passing from top to bottom.

The resulting evaporatively formed, liquid-containing CTA powder was collected on a fabric filter spanning the bottom of the tower, and the solvent-laden air was passed through carbon beds to collect solvent vapours.

The product was transferred from the filter into a steel tray and left exposed as a 1 cm layer in a ventilated hood for 15 minutes to remove residual solvent. Analysis showed 85.2 percent fragrance and 14.8 percent CTA, with less than 1 ppm of methylene chloride.

EXAMPLE 2

A 5 mg sample of this powder placed on the inner left wrist and rubbed gently with the right forefinger was readily distributed over an area of about 3 square centimeters and then completely vanished on further gentle rubbing. Fragrance imparted to the treated skin area persisted until washed after six hours.

No grittiness was observed during this experiment; the mean particle diameter was about 30 microns, and particles larger than 150 microns were not observed.

EXAMPLE 3

The preparation of Example 1 was repeated using as the porogen liquid a composition containing 75% Dow Corning DC-345 cyclic silicone liquid, 15% Adol 66 isostearyl alcohol, and 10% Carruba Women's Perfume Oil #37288. A white powder very similar to that of Example 1 was obtained, which performed on the skin as described in Example 2, except for the formulated difference in fragrance character.

EXAMPLE 4

A sample of the fragrant powder from Example 1 was placed in a small vial with a 3/32" neck opening. With gentle tapping the powder was found to deliver readily onto the wrist from the inverted vial in controllable amounts as small as a few milligrams. The powder so delivered was readily distributed, rubbed, and caused to vanish.

EXAMPLE 5

A sample of the fragrant powder of Example 1 was pressed into a small steel cosmetic tray with a compressive pressure of about 75 PSI. The resulting cake did not fall out of the tray when inverted, nor did it crack or jar loose when dropped from a 12" height onto a smooth hard surface. Visible powder was readily rubbed from the cake using either a fingertip or a sponge-rubber applicator, and such recovered powder readily distributed over the skin and performed thereon as the powder of Example 2.

EXAMPLE 6

The powder of Example 1 was blended with 10% by weight of a cosmetic blend of mica and titania (Mearl TIMICA 110S), the blending operation being conducted in a small vial using a benchtop vortex mixer adjusted barely to fluidize the powder mixture. The resulting powder blend appeared whiter and drier than the original TIMICA-free powder when observed through the walls of the vial. Applied to the skin an gently rubbed, the white powdery appearance was lost, while the TIMICA imparted a faint sparkle to the skin.

EXAMPLE 7

40% by weight of the powder of Example 1 was blended with 60% of Dow Corning 345 cyclic silicone liquid to produce a smooth cream. Rubbed on the skin this produced a pleasant sense of emolliency and left only a slightly moist appearance, which vanished within 5 minutes as the slightly volatile silicone evaporated. A Persistent fragrance was imparted which persisted until washed off after six hours.

EXAMPLE 8

In a sealed container the stabilizer-free cream of Example 7 showed no change in appearance or texture after storage for 60 days at 20°-25° C.

EXAMPLE 9

A 1 gm sample of the powder of Example 1 was kept in a closed vial for 30 days at 20°-25° C. and then compared in odor on the skin with a fresh sample of the liquid perfume blend originally incorporated into the powder. At the same $mg/cm^2$ application level no difference in rendition was detected.

It will be understood that the above description pertains to only several embodiments of the present invention. That is, the description is Provided by way of illustration and not by way of limitation. The invention, therefore, is to be defined according to the following claims.

What is claimed is:

1. A fragrance composition for the delivery of a topical fragrance, the composition comprising a formulation of a frangible, liquid-containing, cellulosic powder formed by spray evaporation and having particles ranging in average diameter from about 1 to about 500 micrometers, the particles further characterized by being microporous with a plurality interconnecting pores ranging in size from about 1 to about 500 nanometers and having a structure which is readily fragmented; and a liquid fragrance preparation loaded within the pores of the powder particles, such that the liquid-containing powder has a liquid content ranging from about 50 percent to 95 percent by weight and, upon application and rubbing, the rubbed particles fragment and the fragrance preparation is readily released.

2. The composition of claim 1 wherein the cellulosic powder is a polymeric powder chosen from the group consisting of cellulose acetates, cellulose butyrates, cellulose nitrates, cellulose propionates, ethyl celluloses, and discrete and molecular mixtures thereof.

3. The composition of claim 1 wherein the composition further comprises an emollient not incorporated within the frangible powder.

4. The composition of claim 1 wherein the fragrance preparation comprises a fragrance compound chosen from the group consisting of esters, alcohols, ketones, and aldehydes, linear, branched or cyclic, saturated or unsaturated, of low, intermediate or high molecular weight, and derivatives and mixtures thereof.

* * * * *